United States Patent
Bang et al.

(10) Patent No.: US 10,786,564 B2
(45) Date of Patent: Sep. 29, 2020

(54) MDCK SUSPENSION CELL LINES IN SERUM-FREE, CHEMICALLY-DEFINED MEDIA FOR VACCINE PRODUCTION

(71) Applicants: NATIONAL HEALTH RESEARCH INSTITUTES, Zhunan Town, Miaoli County (TW); FUJIFILM IRVINE SCIENTIFIC, INC., Santa Ana, CA (US)

(72) Inventors: Jenny Bang, Santa Ana, CA (US); Hsiao-Tzu Ni, Santa Ana, CA (US); Alan Yung-Chih Hu, Zhunan Town (TW); Tsai-Chuan Weng, Zhunan Town (TW)

(73) Assignees: NATIONAL HEALTH RESEARCH INSTITUTES, Zhunan Town, Miaoli County (TW); FUJIFILM IRVINE SCIENTIFIC, INC., Santa Ana, CA (US)

( * ) Notice: Subject to any disclaimer, the term of this patent is extended or adjusted under 35 U.S.C. 154(b) by 152 days.

(21) Appl. No.: 15/771,029

(22) PCT Filed: Oct. 31, 2016

(86) PCT No.: PCT/IB2016/056567
§ 371 (c)(1),
(2) Date: Apr. 25, 2018

(87) PCT Pub. No.: WO2017/072744
PCT Pub. Date: May 4, 2017

(65) Prior Publication Data
US 2018/0311337 A1    Nov. 1, 2018

Related U.S. Application Data

(60) Provisional application No. 62/248,954, filed on Oct. 30, 2015.

(51) Int. Cl.
*C12N 5/00* (2006.01)
*A61K 39/145* (2006.01)
*A61K 39/12* (2006.01)
*C12N 5/071* (2010.01)
*C12N 7/00* (2006.01)
*C12N 15/85* (2006.01)
*A61P 31/16* (2006.01)

(52) U.S. Cl.
CPC ............ *A61K 39/145* (2013.01); *A61K 39/12* (2013.01); *C12N 5/0686* (2013.01); *C12N 7/00* (2013.01); *C12N 15/8509* (2013.01); *A61P 31/16* (2018.01); *C12N 2015/8518* (2013.01); *C12N 2500/90* (2013.01); *C12N 2500/99* (2013.01); *C12N 2511/00* (2013.01); *C12N 2513/00* (2013.01); *C12N 2517/02* (2013.01); *C12N 2760/16034* (2013.01); *C12N 2760/16051* (2013.01); *C12N 2760/16134* (2013.01); *C12N 2760/16151* (2013.01); *C12N 2760/16251* (2013.01)

(58) Field of Classification Search
None
See application file for complete search history.

(56) References Cited

U.S. PATENT DOCUMENTS

| | | | |
|---|---|---|---|
| 10,329,536 B2* | 6/2019 | Vorlop | C12N 7/00 |
| 2012/0115206 A1* | 5/2012 | Schwartz | C12N 7/00 435/236 |
| 2013/0183741 A1* | 7/2013 | Park | C12N 5/0686 435/239 |
| 2015/0353882 A1* | 12/2015 | Ando | C12M 23/48 435/404 |
| 2016/0304928 A1* | 10/2016 | Yang | C12N 5/0018 |

FOREIGN PATENT DOCUMENTS

| | | |
|---|---|---|
| JP | 2000-507448 A | 6/2000 |
| WO | WO-01/64846 A1 | 9/2001 |
| WO | WO-2014/196795 A1 | 12/2014 |

OTHER PUBLICATIONS

A. Yung-Chih Hu et al., "Production of Inactivated Influenza H5N1 Vaccines from MDCK Cells in Serum-Free Medium", PLOS One, vol. 6, No. 1, e14578, Jan. 1, 2011.
Extended European Search Report on EP 16859190.7, dated Jul. 29, 2019.
S. Kluge et al., "Monitoring Changes in Proteome During Stepwise Adaptation of a MDCK Cell Line From Adherence to Growth in Suspension", Elsevier Ltd., vol. 33, No. 35, Aug. 1, 2015, pp. 4269-4280.
PCT International Search Report and the Written Opinion for Application No. PCT/IB2016/056567 dated Apr. 10, 2017. (11 pages).

* cited by examiner

*Primary Examiner* — Catherine S Hibbert
(74) *Attorney, Agent, or Firm* — Foley & Lardner LLP

(57) ABSTRACT

Disclosed is an adapted Madin-Darby canine kidney cell line capable of suspension culture in the absence of serum, and a chemically-defined medium for culture of the adapted MDCK cell line. Further disclosed are culture methods for growing the adapted MDCK cell line and methods for producing a vaccine from the adapted MDCK cell line grown in the chemically-defined medium.

13 Claims, 7 Drawing Sheets

MDCK SUSPENSION CELL LINES IN SERUM-FREE, CHEMICALLY-DEFINED MEDIA FOR VACCINE PRODUCTION

CROSS-REFERENCE TO RELATED APPLICATIONS

This application is a U.S. national stage application of International Patent Application No. PCT/IB2016/056567, filed on Oct. 31, 2016; which claims priority to U.S. Provisional Application No. 62/248,954, filed Oct. 30, 2015; the content of each of these applications is incorporated herein in its entirety by reference.

BACKGROUND

Field

The present invention relates generally to the field of vaccine virus production, and particularly to growth and suspension culture of Madin-Darby canine kidney (MDCK) cell lines in serum-free, chemically-defined medium.

Description of the Related Art

Currently, vaccines are produced using a variety of methods, including culture in chicken eggs, primary cells, or cell lines. These methods involve numerous problems with respect to costs, risks, and ability to maintain large-scale, industrial production levels.

Madin-Darby canine kidney (MDCK) cells are one cell line used for vaccine production, particularly for influenza vaccines. Cell culture for vaccine production is advantageous over chicken eggs because cell culture does not rely on the availability of eggs and can be performed on a larger scale. However, there are several drawbacks to the culture of MDCK cells. MDCK cells require undefined supplement, such as serum for culture, which is expensive and undesirable when making pharmaceutical products for human use. MDCK cells also require frequent media changes, further increasing cost. Furthermore, MDCK cells grow in adherent culture, either on the culture vessel, which requires significant surface area; or on microcarriers, which are not cost effective, are labor intensive, and pose a risk of damaging the cells.

U.S. Pat. Nos. 6,825,036 and 8,846,932; and U.S. Patent Application Publication No. 2013/0183741 describe methods and MDCK cell lines for serum-free suspension culture and vaccine production. However, growth of these cells in serum-free culture medium required hydrolysate or other animal-derived components, which is an undefined media component that represents a disadvantage in cost and controllability.

Accordingly, there remains a need for MDCK cell lines capable of suspension culture in serum-free and chemically-defined media for efficient vaccine production.

SUMMARY OF THE INVENTION

The technology described herein relates to adapted MDCK cells and culture medium for growing the cells. The technology further relates to methods of culturing the cells and methods for producing vaccines using the adapted cells. The adapted MDCK cells as described herein have been adapted to serum-free suspension culture without the use of microcarriers. The adapted MDCK cells are further cultured in the presence of a chemically-defined medium as described herein.

The MDCK cell line is an adherent cell line derived from the kidney of a normal female adult Cocker Spaniel. MDCK cells are used for virus production, e.g. to produce vaccines. Currently, MDCK cells are cultured in serum-containing medium as adherent cultures. In order to grow MDCK cells to a density that is suitable for commercial production, microcarriers (e.g., microbeads) or roller-bottles are used to increase the surface area for MDCK cell growth. Microcarrier or roller-bottle culture of MDCK has numerous drawbacks, including increased expense and limitation of scalability.

Cell lines, including MDCK cells, are conventionally grown in serum-containing media to aid growth and proliferation of the cells. However, serum is not advantageous, particularly in large-scale commercial production, due to its high cost, risk of contamination, undefined nature, and variability. Such disadvantages spurred the use of serum-free medium for culturing some cell lines. However, serum-free medium still contains animal components, e.g. transferrin, and other undefined products, e.g. hydrolysate, which provide a level of risk and uncertainty when using such medium.

Chemically-defined medium, which contains only recombinant proteins and/or hormones and for which the precise medium constituents and concentrations are known, provides an improved system for growth of cell lines used in commercial production of viruses for vaccines. Chemically defined medium does not contain any animal-derived ingredients.

The ability of a given cell line to grow in serum free, chemically-defined medium is unpredictable. The adaptation of a cell line to suspension growth, particularly in a given medium, is similarly unpredictable. For example, cells may die off when they are grown in suspension culture without the opportunity to adhere to a surface; cells may die off when serum is removed from the medium; chemically defined medium may not be sufficient to sustain growth of the cells; cell growth and/or proliferation may be negatively affected (e.g., by lengthening doubling time); cell morphology and/or gene expression may be altered such that the cells are no longer suitable for their intended purpose; characteristics of the cells may be altered such that virus made by the cells is insufficiently antigenic to be used in a vaccine; and so forth.

The disclosure herein is predicated, in part, on the surprising discovery that MDCK cells can be adapted to suspension growth in serum free, chemically-defined medium, and that the adapted MDCK cells produce higher titers of virus for vaccine production than the parental cell line, which is adherent and cultured in the presence of serum, and the viruses produced by the adapted cells maintain antigenicity.

In one aspect, this disclosure relates to a composition comprising adapted MDCK cells and a growth medium, the growth medium comprising a chemically-defined and animal component free medium, wherein the adapted MDCK cells are maintained in suspension culture without microcarriers.

In one aspect, this disclosure relates to a method for culturing an adapted MDCK cell line in suspension without microcarriers, the method comprising contacting the adapted MDCK cell line with a chemically-defined and animal component free growth medium, wherein the adapted MDCK cell line is capable of growing in suspension culture without microcarriers. In one embodiment, the cells are grown in the presence of 5% $CO_2$. In a preferred embodiment, the medium is not exchanged during cell culture stage.

In one aspect, this disclosure relates to a method for producing a vaccine in an adapted MDCK cell line, said MDCK cell line being capable of being cultured in suspension without microcarriers, said method comprising contacting the MDCK cell line with a chemically-defined and animal component free growth medium. In one embodiment, MDCK cells are inoculated at a concentration of $2 \times 10^5$ cells/ml and virus infection is conducted when the cells approaching stationary phase, as the cell density reaches about $2 \times 10^6$ cells/mL. In one embodiment, before virus infection, media is 100% refreshed by centrifugation, and then tosyl phenylalanyl chloromethyl ketone (TPCK)-trypsin and strain virus are added. In one embodiment, during virus infection stage, cells are incubated at 32-34° C. In one embodiment, the cells are grown in spinner flasks. In one embodiment, the supernatants are harvested when total CPE occurs. In one embodiment, additional glucose is not added to the medium. In one embodiment, the medium contains about 20 mM to about 30 mM glucose, and preferably about 25 mM to about 30 mM glucose, and more preferably about 26 mM to about 28 mM glucose.

In one aspect, this disclosure relates to a method for producing an adapted MDCK cell line that is capable of being cultured in suspension without microcarriers in a chemically-defined medium without serum, said method comprising:
 a) providing an adherent MDCK cell line;
 b) culturing the adherent MDCK cell line in a growth medium comprising 5% (volume/volume, v/v) serum with agitation and in the absence of microcarriers for a period of time sufficient for the MDCK cell line to adapt to suspension culture; and
 c) culturing the suspension-adapted MDCK cell line in suspension culture in a chemically-defined medium without serum, thereby providing an adapted MDCK cell line that is capable of being cultured in suspension without microcarriers in a chemically-defined medium without serum.

In one embodiment, step c) includes: culturing the suspension-adapted MDCK cell line in suspension culture with an increasing amount of a chemically-defined medium and a decreasing amount of serum (v/v) until the chemically-defined medium represents substantially all of the medium in the culture and substantially all of the serum has been removed, thereby providing an adapted MDCK cell line that is capable of being cultured in suspension without microcarriers in a chemically-defined medium without serum.

In one embodiment, the adapted MDCK cell line is cultured in the presence of 5% $CO_2$ in steps b) and c).

In certain embodiments, the adapted MDCK cells have an average doubling time of between about 30 hours and about 35 hours.

In certain embodiments, the adapted MDCK cells are suitable for producing virus for a human vaccine. In certain embodiments, the virus produced by the adapted MDCK cells is antigenic. In preferred embodiments, the virus is an influenza virus.

In certain embodiments, the adapted MDCK cells are the cells as deposited with Leibniz-Institut DSMZ-Deutsche Sammlung von Mikro-organismen and Zellkulturen GmbH (InhoffenstraBe 7 B, 3 8124 Braunschweig, Germany) as deposit number DSM ACC3309 on Oct. 21, 2016.

DETAILED DESCRIPTION

Figure 1:
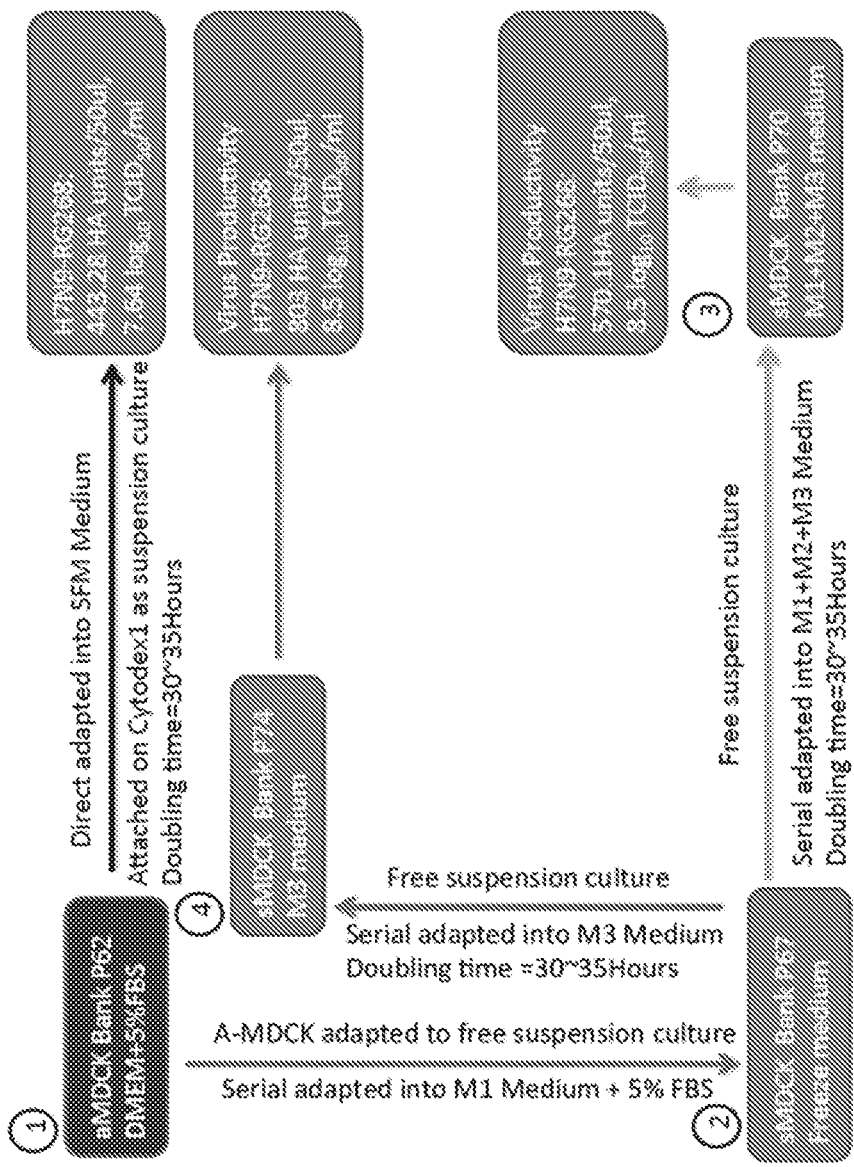
FIG. 1 is an overview of the protocol used to adapt the MDCK cells for suspension culture in chemically-defined, serum-free media.

After reading this description it will become apparent to one skilled in the art how to implement the invention in various alternative embodiments and alternative applications. However, all the various embodiments of the present invention will not be described herein. It will be understood that the embodiments presented here are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description of the invention is divided into various sections only for the reader's convenience and disclosure found in any section may be combined with that in another section. Unless defined otherwise, all technical and scientific terms used herein have the same meaning as commonly understood by one of ordinary skill in the art to which this invention belongs.

In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

The term "about" when used before a numerical designation, e.g., temperature, time, amount, concentration, and such other, including a range, indicates approximations which may vary by (+) or (−) 10%, 5% or 1%.

As used herein, the term "Madin-Darby canine kidney cells" or "MDCK cells" refers to cells from a cell line derived from the tissue of an apparently normal adult female cocker spaniel in 1958. MDCK cells are often used for vaccine production, particularly influenza. MDCK cells are commercially available, for example from BCRC (catalogue no. 60004, derived from ATCC CCL-34). Commercially available MDCK cells are adherent in culture and require serum for optimal growth.

As used herein, the term "adapted MDCK cells" refers to cells that have been adapted to grow in suspension culture (without microcarriers) in chemically-defined medium, without serum.

As used herein, the term "chemically defined medium" refers to cell culture medium in which all of the components are known, as are their exact concentrations. Chemically defined medium contains no animal-derived components.

As used herein, the term "adherent culture" refers to cell culture wherein the cells adhere to a surface, e.g. a tissue culture plate or microcarrier. "Microcarriers" are any carrier, e.g. beads, that provides a surface for cells to adhere other than the surface of the culture vessel.

As used herein, the term "suspension culture" refers to cell culture in suspension, as opposed to adherent culture, without the use of microcarriers.

As used herein, the term "substantially all," for example when referring to the reduction of serum and/or growth medium in a culture, means that the undesired component comprises less than about 0.1% of the culture medium, and preferably less than about 0.05%, and more preferably less than about 0.01%. In a most preferred embodiment, all of the undesired component is removed from the culture medium. Similarly, the desired component comprises more than about 99.90%, preferably more than about 99.95%, and more preferably more than about 99.99%. In a most preferred embodiment, the desired component (e.g., chemically defined medium) comprises 100% of the medium.

Compositions

The present disclosure relates to compositions comprising adapted MDCK cells and a chemically-defined growth medium. The composition does not comprise serum or other animal-derived components.

Adapted MDCK Cell Lines

In one aspect, the present disclosure relates to adapted MDCK cells that are capable of growth and/or proliferation without serum in chemically-defined medium in suspension culture. The adapted MDCK cells do not require a surface (e.g. microcarriers) for growth or proliferation in suspension culture. The cells can be used to produce virus for vaccine production.

In some embodiments, the adapted MDCK cells have an average doubling time of between about 20 hours and about 40 hours. In some embodiments, the adapted MDCK cells have an average doubling time of between about 25 hours and about 40 hours. In some embodiments, the adapted MDCK cells have an average doubling time of between about 30 hours and about 40 hours. In some embodiments, the adapted MDCK cells have an average doubling time of between about 35 hours and about 40 hours. In some embodiments, the adapted MDCK cells have an average doubling time of between about 20 hours and about 35 hours. In some embodiments, the adapted MDCK cells have an average doubling time of between about 20 hours and about 30 hours. In a preferred embodiment, the adapted MDCK cells have an average doubling time of between about 30 hours and about 35 hours.

In some preferred embodiments, the adapted MDCK cells are suitable for producing virus for a human vaccine. Viruses that can be produced in the adapted MDCK cells include, without limitation, A/Vietnam/1194/04 (H5N1) virus (NI-BRG-14) and A/Anhui/1/2013 (H7N9) virus (NIBRG-268) are used as examples. In an especially preferred embodiment, the virus is an influenza virus. In an especially preferred embodiment, the vaccine is a human vaccine.

In one embodiment, the virus produced by the adapted MDCK cells retains antigenicity. In one embodiment, the virus is capable of causing an immune reaction in a host cell or organism. In a preferred embodiment, the host cell or organism is a human cell or a human.

In certain embodiments, the adapted MOCK cells are the cells as deposited with Leibniz-Institut DSMZ-Deutsche Sammlung von Mikro-organismen and Zellkulturen GmbH as deposit number DSM ACC3309 on Oct. 21, 2016. The cells were submitted for deposit on Oct. 19, 2016.

Chemically Defined Medium for Culture of Suspension Adapted MDCK Cell Lines

The chemically-defined medium can be any chemically-defined medium that does not contain serum, hydrolysates, or other animal-derived components. In a preferred embodiment, the chemically-defined medium is BALANCD® Simple MDCK (Irvine Scientific, catalog ID: 91136). In some embodiments, the chemically-defined medium comprises one or more of the amino acids as set forth in Table 1. In some embodiments, the amino acid(s) are present in the medium at a concentration within the range(s) set forth in Table 1. The concentration may be any subrange or value within a given range, including endpoints. In some embodiments, one or more amino acids is present in the medium at the preferred concentration provided in Table 1.

TABLE 1

Example Amino Acid Constituents of Chemically-Defined Medium

| Description | Conc. Range (mM) | Preferred Conc. (mM) |
|---|---|---|
| L-SERINE | 0.1-5 | 1.1114 |
| L-ARGININE HCl | 0.1-5 | 1.1193 |
| L-LEUCINE | 0.05-4 | 0.7192 |
| L-TYROSINE 2Na•2H2O | 0.05-4 | 0.3419 |
| L-ISOLEUCINE | 0.05-4 | 0.6632 |
| L-THREONINE | 0.05-4 | 0.7194 |
| L-VALINE | 0.05-4 | 0.7196 |
| L-CYSTEINE HCl•H2O | 0.05-4 | 0.4555 |
| L-Aspartic Acid | 0.05-4 | 0.5770 |
| L-Glutamic Acid | 0.05-4 | 0.4894 |
| L-ASPARAGINE | 0.05-4 | 0.4050 |
| L-PHENYLALANINE | 0.05-4 | 0.3437 |
| L-HISTIDINE HCl H2O | 0.02-2 | 0.2403 |
| L-Methionine | 0.02-2 | 0.1848 |
| L-ALANINE | 0.02-2 | 0.2694 |
| L-TRYPTOPHAN | 0.02-2 | 0.0707 |

In some embodiments, the chemically-defined medium comprises glucose. In some embodiments, the concentration of glucose is between about 20 mM and about 30 mM. In a preferred embodiment, glucose is present at a concentration of about 25 mM to about 30 mM. In an especially preferred embodiment, glucose is present at a concentration of about 27.75 mM. The concentration may be any range or value within the ranges recited herein, including endpoints.

Methods of Making and Culturing Suspension-Adapted MDCK Cells

The present disclosure relates to methods of making and/or culturing MDCK cells/cell line in a chemically-defined, serum-free medium. The MDCK cells are cultured in suspension and do not require adhesion to a culture vessel or microcarriers.

Making Suspension Adapted MDCK Cell Lines

In one aspect, the current disclosure relates to a method for making a suspension-adapted MDCK cell line (MDCK cells) that is capable of growth and/or proliferation in a chemically-defined medium.

In some embodiments, this disclosure relates to method for producing adapted MDCK cells (cell line) that is capable of being cultured in suspension without microcarriers in a chemically-defined medium without serum, said method comprising:

a) providing adherent MDCK cells;
b) culturing the adherent MDCK cells in a growth medium comprising serum and in the absence of microcarriers for a period of time sufficient for the MDCK cells to adapt to suspension culture to produce suspension-adapted MDCK cells; and
c) culturing the suspension-adapted MDCK cells in suspension culture in a chemically-defined medium without serum, thereby providing MDCK cells that are capable of being cultured in suspension without microcarriers in a chemically-defined medium.

In one embodiment, the growth medium of step b) is not a chemically-defined medium. In one embodiment, the chemically-defined medium is BALANCD® Simple MDCK medium.

In one embodiment, the cells are grown in a stirred bioreactor.

In one embodiment, step c) includes: culturing the suspension-adapted MDCK cell line in suspension culture with an increasing amount of a chemically-defined medium and a decreasing amount of serum (v/v) until the chemically-defined medium represents substantially all of the medium in the culture and substantially all of the serum has been removed, thereby providing an adapted MDCK cell line that is capable of being cultured in suspension without microcarriers in a chemically-defined medium without serum.

In one embodiment, the MDCK cells are cultured in about 1% to about 20% serum in step b). In one embodiment, the MDCK cells are cultured in about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% serum in step b). Ranges include any ranges or values between any two values recited herein, including sub-ranges. In a preferred embodiment, the MDCK cells are cultured in about 2% to about 10% serum in step b). In an especially preferred embodiment, the MDCK cells are cultured in about 2% to about 5% serum in step b).

In one embodiment, step c) involves removing at least a portion of the medium from the cell culture and replacing the removed medium with chemically-defined medium. In one embodiment, step c) involves separating MDCK cells from the removed medium and transferring the separated cells back to the MDCK culture. In one embodiment, step c) involves increasing the portion of chemically defined medium with passages. In one embodiment, step c) involves directly adapting the cells into serum-free, chemically defined medium.

In a preferred embodiment, the serum-free, chemically-defined medium is BALANCD® Simple MDCK medium.

Culturing Suspension-Adapted MDCK Cell Lines

In one aspect, the current disclosure relates to a method for culturing Madin-Darby canine kidney (MDCK) cells in suspension without microcarriers. In one embodiment, the method comprises contacting the suspension-adapted MDCK cells with a chemically-defined medium. In preferred embodiments, no serum or other animal-derived components are present in the growth medium. In one embodiment, the cells are grown at 5% $CO_2$. In one embodiment, the cells are passaged approximately every 3-5 days. Preferably, the cells are passaged approximately every 4 days. In an especially preferred embodiment, the medium is not changed during culture (e.g., once the cells have been established in culture).

In preferred embodiments, the suspension-adapted MDCK cells are grown under conditions that maintain the cells in suspension (e.g. agitation). Such conditions are known in the art. Non-limiting examples include single-use stirred-tank reactor, wave bioreactor, spinner flasks, and shaking flasks.

Methods of Preparing Vaccines

When virus productivity from MDCK cells is optimized, it is unpredictable whether the virus produced from the cells will maintain similar antigenicity to the virus produced by unmodified cells or protocols. The present disclosure relates to methods of producing virus for vaccines using the compositions and culture methods described herein. In preferred embodiments, the antigenicity of the virus is maintained. In one embodiment, the disclosure relates to a method for producing a vaccine in MDCK cells, said MDCK cells being capable of being cultured in suspension without microcarriers and without serum. In a preferred embodiment, the cells are cultured in a chemically-defined medium. In one embodiment, the chemically-defined medium is BALANCD® Simple MDCK medium.

In some embodiments, additional glucose is not added to the medium during vaccine production.

In some embodiments, the medium is not exchanged during the cell culture stage (e.g., after the cells are established in culture). Currently, at least a portion of the growth medium of MDCK cells used for during the cell culture stage is removed and replaced daily during the cell culture stage Eliminating this step offers significant benefits, including a reduction in the amount of medium used (and over-all cost of the process), reduction in the processing steps, etc.

In some embodiments, antigenicity of the virus produced by the MDCK cells is evaluated. In preferred embodiments, the virus maintains antigenicity. In some embodiments, the virus maintains antigenicity relative to virus produced by adherent MDCK cells. In some embodiments, the virus maintains antigenicity with respect to the required antigenicity for production of the desired vaccine. In some embodiments, the virus maintains antigenicity with respect to cells or an organism. In some embodiments, the cells are human cells. In some embodiments, the organism is a human.

"Maintaining antigenicity" refers to the ability of the virus (or portion of a virus) produced by the MDCK cells to induce an immune response, e.g. in a cell or an organism. Antigenicity can be measured by any method, e.g. HI assay.

EXAMPLES

Additional embodiments are disclosed in further detail in the following examples, which are not in any way intended to limit the scope of the claims.

Example 1: Adaptation of MDCK Cells to Suspension Culture in Chemically-Defined, Serum-Free Medium A schematic of one, non-limiting example protocol for adaptation of adherent MDCK cells to serum-free suspension culture is provided in FIG. 1. Briefly, adherent MDCK cells (aMDCK) (1) were serially adapted into suspension culture using medium containing 5% (v/v) fetal bovine serum (FBS) (2). Suspension-adapted MDCK cells (sMDCK) were then adapted into serum-free BALANCD® Simple MDCK medium (Irvine Scientific) (3). aMDCK cells, grown on CYTODEX™ 1 beads (GE Life Sciences), were also adapted into serum-free medium, without adaptation to suspension culture. Virus productivity and doubling time is provided for each condition.

Prior to adaption of the aMDCK cells into suspension culture, MDCK cells were initiated as adherent cultures from a frozen working cell bank of cells growing in Dulbecco's Modified Eagle Medium (DMEM) with 5% FBS. The cells were passaged several times in T-flasks and serial adapted into medium containing 5% FBS. That is, the concentration of DMEM in the growth medium was slowly decreased and the concentration of BALANCD® Simple MDCK medium was slowly increased over time until substantially all of the growth medium in the T-flask comprised BALANCD® Simple MDCK medium.

Cells in the T-flasks were trypsinized using Trypsin-EDTA, and then the cells were centrifuged at 1000 rpm (200 g) to remove the trypsin. The cells were resuspended in fresh medium containing 5% FBS and were seeded in 125 mL spinner flasks at $5 \times 10^5$ cells/mL in a total volume of 60 mL. Spinner flasks were placed on a stir plate (45~55 rpm) in a 37° C., humidified incubator with 5% $CO_2$. MDCK suspension cultures were refreshed with 33% BALANCD® Simple MDCK medium containing 5% FBS every 3-4 days. The cell density declined to approximately $1 \times 10^5$ to $2 \times 10^5$ cells/mL within one week, and the viability was above 50%. MDCK cells started to grow at the second or third week. Doubling times in MDCK suspension cultures were similar to those seen in adherent microcarrier cultures (30-40 hours) and the cells grew in single-cell suspension (i.e. minimal aggregation). Maximum MDCK cell densities in suspension cultures are approximately $2 \times 10^6$ cells/mL with viabilities >90%. These suspension-adapted MDCK cells were frozen in serum-free medium with 10% DMSO as a master cell bank.

The suspension-adapted MDCK cells from the frozen master cell bank were thawed and directly initiated as suspension cultures in BALANCD® Simple MDCK medium containing 5% FBS. At the second passage after thawing, the cells were directly adapted into completely serum-free BALANCD® Simple MDCK medium. At the third passage after thawing, the cells were frozen in serum-free medium with 10% DMSO to create a working cell bank.

The suspension-adapted, serum free-adapted MDCK cells (sMDCK) from the frozen working cell bank were thawed and directly initiated as suspension cultures in BALANCD® Simple MDCK, without serum. Maximum sMDCK cell densities in suspension cultures were approximately $2 \times 10^6$ cells/mL with viabilities >90%. Doubling time for sMDCK was 30-40 hours. Cells were grown in spinner culture at approximately 50 to 70 rpm in 5% $CO_2$.

Example 2: Aggregation of MDCK Cells

Figure 2A:
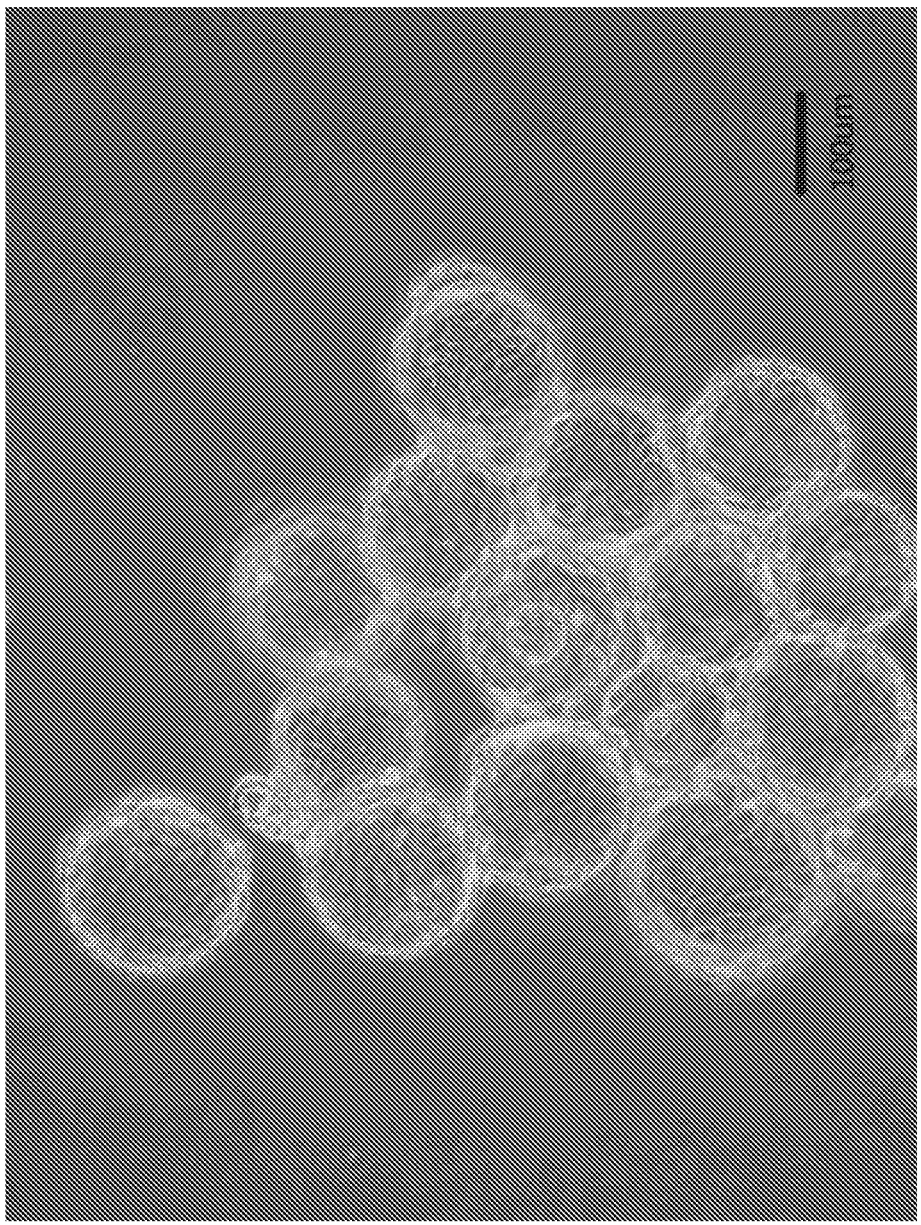
FIG. 2A is photomicrograph of adherent MDCK (aMDCK) cells attached to microcarriers. Cells were cultured in serum-free medium.
Figure 2B:
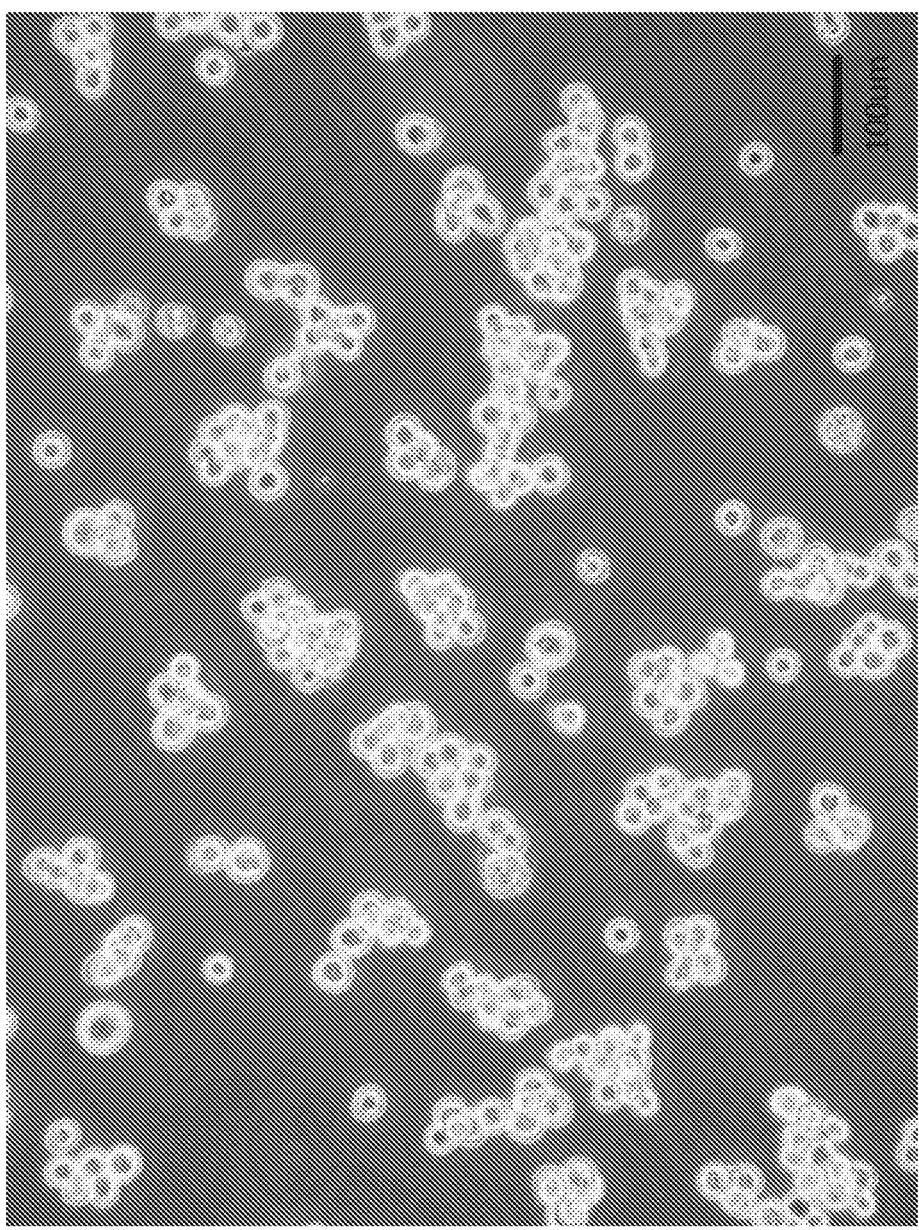
FIG. 2B is photomicrograph of adapted MDCK (sMDCK) cells grown without microcarriers. Cells were cultured in chemically-defined, animal component-free medium.

FIG. 2A shows a photo micrograph of aMDCK cells attached to Cytodex1 beads in serum-free culture. FIG. 2B shows a photo micrograph of sMDCK cells in free suspension culture in serum-free BALANCD® Simple MDCK.

This level of aggregation was obtained without the use of pipetting or other methods of mechanically dispersing the cells (other than the 50 rpm spinner speed required for culture of the cells). Without being bound by theory, it is believed that reducing cell aggregation provides a greater exposed cell surface area and allows for better infection of the cells, thereby resulting in a higher viral titer.

Example 3: MDCK Cell Growth Comparison

Growth rates of MDCK cells were evaluated. MDCK cells were seeded into 125 mL spinner flasks at a density of $0.2 \times 10^6$ cells/mL to $0.25 \times 10^6$ cells/mL and grown in an incubator at 37° C. and 5% $CO_2$ at a spinner speed of 50 rotations per minute (rpm). Cells were passaged every four days. sMDCK cells were cultured in BALANCD® Simple MDCK medium (Irvine Scientific) supplemented with 4 mM L-glutamine, without microcarriers. aMDCK cells were grown in OPTIPRO™ SFM (Life Technologies) supplemented with 4 mM L-glutamine, attached to 5 g/L CYTODEX® 1 beads (GE Healthcare). Starting on day 2 of culture, 70% of the culture medium from the aMDCK cells was removed and replaced with fresh medium. No media exchange was performed for sMDCK cells.

Figure 3:
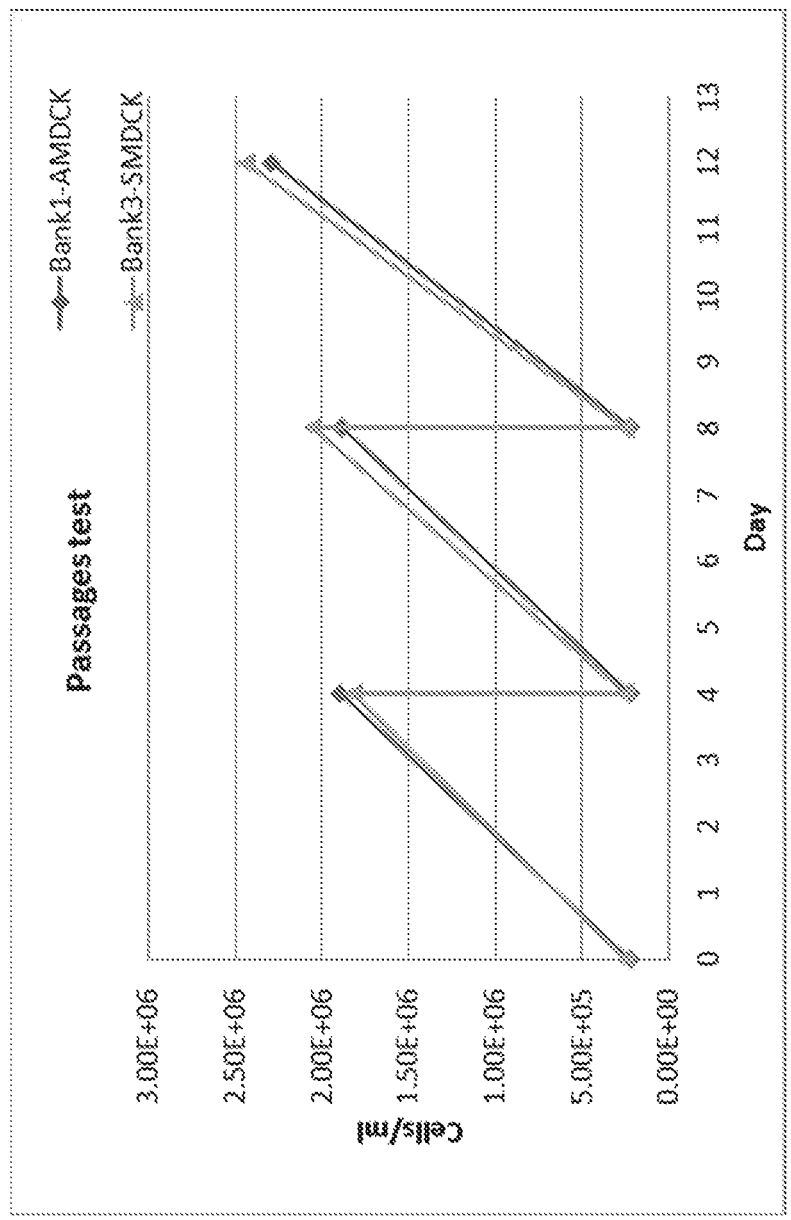
FIG. 3 shows the viable cell density over time of cultures of aMDCK cells (♦) versus sMDCK cells (▲).

FIG. 3 shows the growth rates of the two cell lines over twelve days of culture. Viable cell density reached ~$2 \times 10^6$ cells/mL in 4 days, a similar growth pattern compared to the microcarrier culture. No significant change in growth rate was observed.

No medium exchange was necessary for the suspension culture. In contrast, microcarrier culture required a daily media change of 70%, starting on day 2 of culture to reach high cell density.

Example 4: Influenza Virus Production in sMDCK Cells

The ability of the sMDCK cells to produce virus was determined. MDCK cells were seeded into 125 mL spinner flasks at a density of $0.2 \times 10^6$ cells/mL to $0.25 \times 10^6$ cells/mL and grown as described in Example 3. No additional glucose was added to the medium.

Once the cells reached a density of $2 \times 10^6$ cells/mL, medium was first 100% refreshed by centrifugation. TPCK-trypsin was added into culture medium and then cells were infected with H7N9 influenza virus at low multiplicity of infection (MOI). During virus culture stage, spinner flasks were incubated at 34° C. The supernatants were harvested when total cytopathic effect (CPE) occurred.

Figure 4:
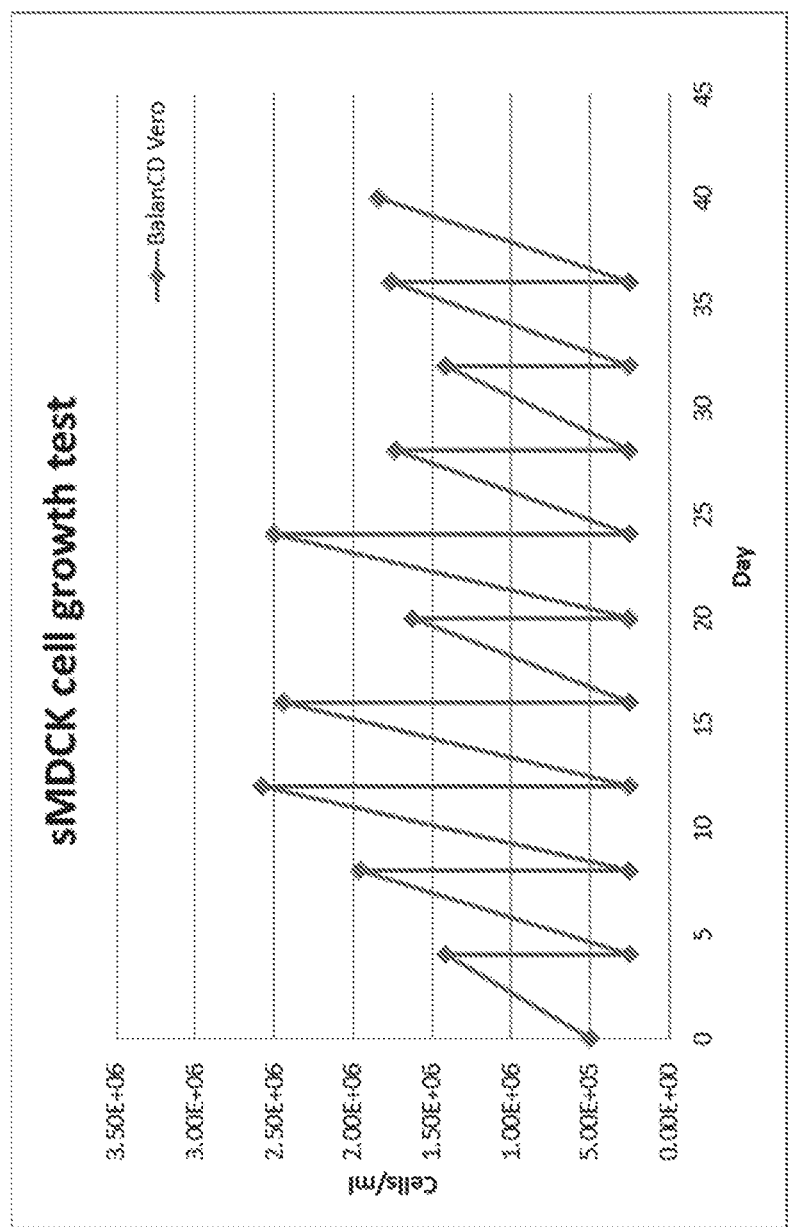
FIG. 4 shows the results of a sMDCK cell growth test over ten passages.
Figure 5:
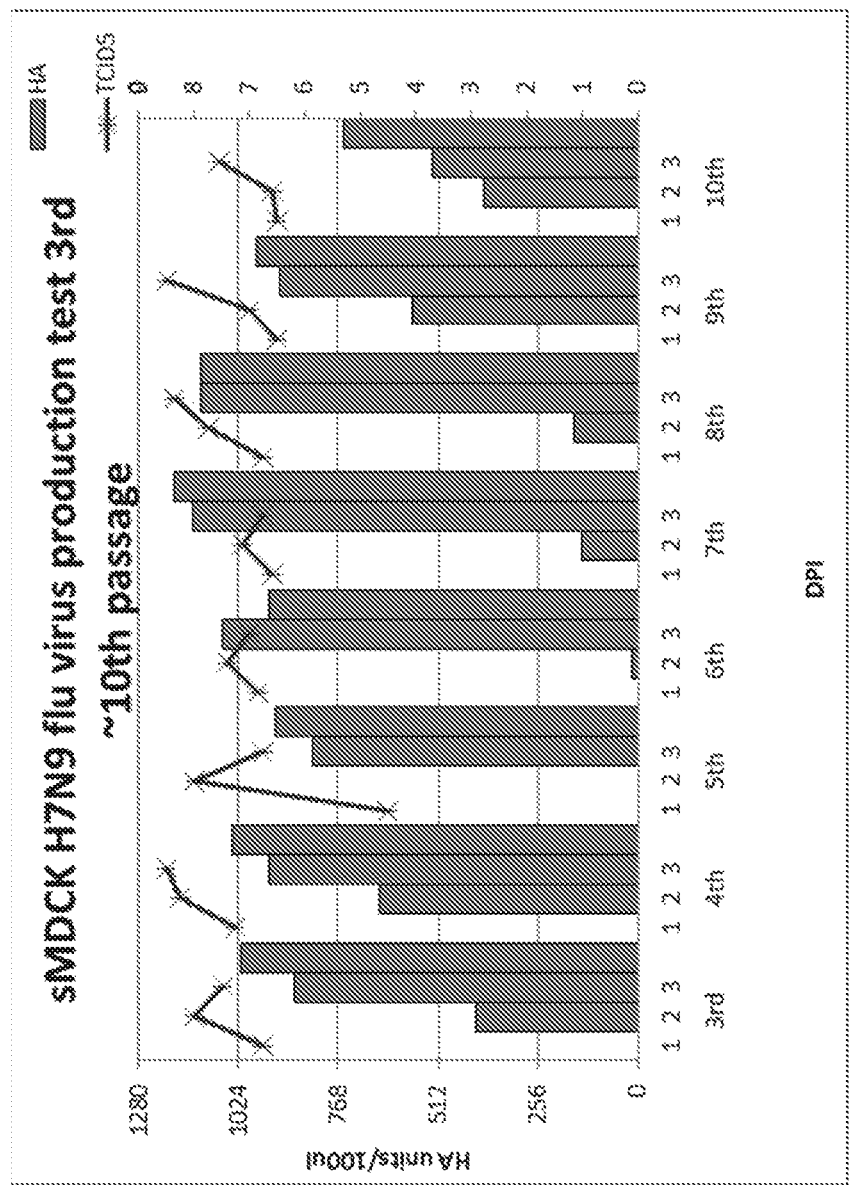
FIG. 5 shows the results of a H7N9 flu virus production test performed during several passages ($3^{rd}$ through $10^{th}$) of the sMDCK cells.
Figure 6:
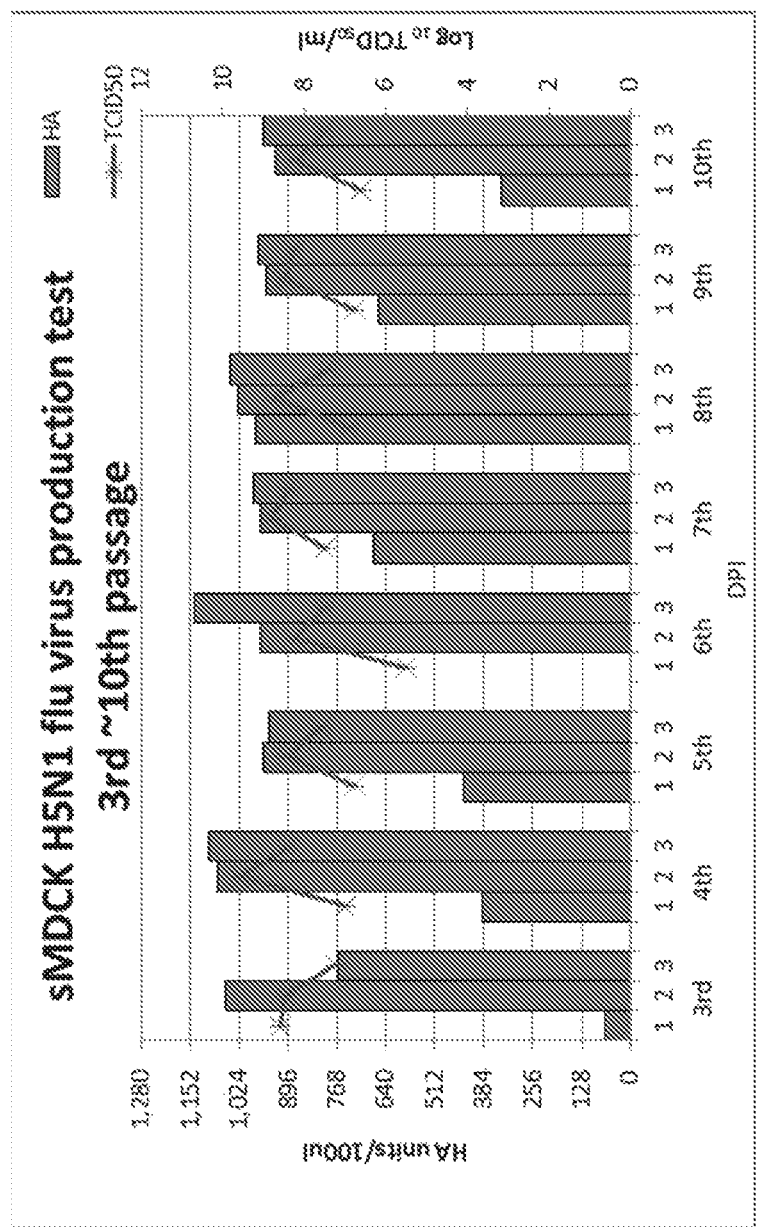
FIG. 6 shows the results of a H5N1 flu virus production test performed during several passages ($3^{rd}$ through $10^{th}$) of the sMDCK cells.

Maximum sMDCK cell densities in suspension cultures are approximately $2 \times 10^6$ cells/mL with viabilities >90%. Doubling times in sMDCK are 30-40 hours and the cells grow in aggregated-cell suspension (FIG. 4). For each sample, two serial 1:2 dilutions (12×100 µl each) were prepared in round bottomed 96-well microtiter plates. Serial dilutions were shifted by a factor of $1:2^{0.5}$ resulting in a dilution factor of $1:2^{0.5}$ from well to well. One hundred microliters of 0.25% turkey erythrocytes ($2 \times 10^7$ RBC/mL)

were added to each well and plates were incubated at room temperature for at least 2 hours up to one day. Afterwards, plates were scanned with a plated photometer measuring extinction at 700 nm. The transition from carpet-like sedimentation of erythrocytes (in the presence of negligible virus) could be detected as an increase in extinction levels. A Boltzmann sigmoid was fitted to each data set and the dilution at the point of inflection (one of the parameters) was defined as the endpoint of the titration; the inverse of the dilution was defined as the specific HA activity with units 1 HAU $(100 \ \mu L)^{-1}$. An internal standard was used to compensate for fluctuations caused by the varying quality of turkey erythrocytes. Samples belonging to the same experiment were analyzed in the same assay run whenever possible. Statistical analysis of multiply determined samples predicted an analytical error <15% (confidence interval, alpha=0.05) for measurements.

The infectious virus titer was measured by determining the tissue culture infective dose required to infect 50% of MDCK cells. Tenfold serial dilutions ($10^{-1}$ to $10^{-8}$) of the virus samples were prepared in medium containing TPCK-trypsin and inoculated (six replicates per dilution) in 96-well plates grown to confluence with MDCK cells. Plates were incubated at 34° C. for 4 to 7 days. The wells with live cells or with CPE were calculated in each dilution. The TCID50 titer was further calculated by Reed-Muench Method The results are summarized in Table 2. sMDCK cells provided a higher titer than aMDCK cells.

TABLE 2

| H7N9 Production: Peak virus titer during virus propagation stage | | |
|---|---|---|
| | HA (units/100 μl) | TCID$_{50}$/mL |
| aMDCK microcarrier culture | 574.9 ± 113.54 | 7.6 ± 0.10 |
| sMDCK suspension culture | 996.3 ± 113.88 | 7.91 ± 0.52 | aMDCK cells cultured in BALANCD® Simple MDCK medium had a slightly higher titer (512.0 HA units/100 μl) than aMDCK cells cultured in OPTIPRO™ SFM, but still significantly less than the sMDCK cells cultured in BALANCD® Simple MDCK medium. Similar results were observed with H5N1 influenza virus.

H7N9 production test was performed during the 3$^{rd}$ passage to the 10$^{th}$ passage. The virus productivity of sMDCK remained at a high level from the 3$^{rd}$ to 10$^{th}$ passages (FIG. 5). The average HA titer was 989.87 HA units/100 μL and the TCID50 titer was 8.6 $TCID_{50}$/mL (Table 3). Similar results were observed with H5N1 influenza virus (FIG. 6).

TABLE 3

H7N9 Production The peak virus titer during virus propagation stage

| | HA (units/100 μl) | $TCID_{50}$/mL |
|---|---|---|
| aMDCK microcarrier culture | 612.72 | 8.6 |
| sMDCK suspension culture | 989.87 ± 115.89 | 8.63 ± 0.44 |

Example 5: Antigenicity Testing

Antigenicity analysis of the influenza viruses from Example 4 was carried out by hemagglutination (HI) assay using the standard antibody that was purchased from the National Institute for Biological Standards and Control (NIBSC). The HI assay started at a serum dilution of 1:40. Each sample was performed in triplicate.

Influenza viruses were diluted to give a preparation with 8 HAU per 50 ul. The antibody was several diluted in a V-shaped microtiter plate and then 25 ul virus samples were added into microplate. After gentle agitation, the plates were incubated for 15 min at room temperature. The 50 μL of a 0.5% suspension of Turkey red blood cells were added to each well and the plates were left another 30 min before reading. The reciprocal value of the highest dilution of antibody which completely inhibited hemagglutination was determined to be the HI titer. Results are provided in Table 4.

TABLE 4

HI test

| Virus strain | HI titer | Virus strain | HI titer |
|---|---|---|---|
| NIBRG14 | 320 | NIBRG268 | 640 |
| Spinner flask (the 10$^{th}$ passage of sMDCK) | 320 | Spinner flask (the 10$^{th}$ passage of sMDCK) | 640 |

It will be understood by those of skill in the art that numerous and various modifications can be made without departing from the spirit of the present disclosure. Therefore, it should be clearly understood that the forms disclosed herein are illustrative only and are not intended to limit the scope of the present disclosure.

What is claimed is:

1. A composition comprising adapted Madin-Darby canine kidney (MDCK) cells and a growth medium, the growth medium comprising a chemically-defined and animal component free medium, wherein the adapted MDCK cells are in suspension culture without microcarriers, wherein the chemically defined medium sustains cell growth and expansion without medium exchange or subculture, further wherein the adapted MDCK cells are deposited as DSM ACC3309 with Leibniz-Institut DSMZ-Deutsche Sammlung von Mikro-organismen and Zellkulturen GmbH.

2. The composition of claim 1, wherein the adapted MDCK cells have an average doubling time of between about 30 hours and about 35 hours.

3. The composition of claim 1, wherein the adapted MDCK cells are suitable for producing a virus for a vaccine, further wherein the virus maintains antigenicity.

4. A method for producing a virus for vaccine production in adapted Madin-Darby canine kidney (MDCK) cells, said adapted MDCK cells being capable of being cultured in suspension without microcarriers, said method comprising contacting the adapted MDCK cells with a chemically-defined and animal component free growth medium, infecting the cells with a virus, and harvesting the virus, wherein the chemically defined medium sustains cell growth and expansion without medium exchange or subculture, and further wherein the adapted MDCK cells are deposited as DSM ACC3309 with Leibniz-Institut DSMZ-Deutsche Sammlung von Mikro-organismen and Zellkulturen GmbH.

5. A method for producing Madin-Darby canine kidney (MDCK) cells that are capable of being cultured in suspension without microcarriers in a chemically-defined medium without serum, said method comprising:

a) providing adherent MDCK cells;

b) culturing the adherent MDCK cells in a growth medium comprising serum in a stirred bioreactor and in the absence of microcarriers for a period of time sufficient for the MDCK cells to adapt to suspension culture; and c) culturing the suspension-adapted MDCK cells in suspension culture in a chemically-defined medium and without serum, thereby providing MDCK cells that are capable of being cultured in suspension without microcarriers in a chemically-defined medium without serum, wherein the chemically defined medium sustains cell growth and expansion without medium exchange or subculture, further wherein the adapted MDCK cells are deposited as DSM ACC3309 with Leibniz-Institut DSMZ-Deutsche Sammlung von Mikro-organismen and Zellkulturen GmbH.

6. The method of claim 5, wherein the growth medium comprises between about 1% and about 10% serum.

7. The method of claim 6, wherein the growth medium comprises about 5% serum.

8. The method of claim 5, wherein the MDCK cells are cultured in the presence of 5% $CO_2$ in steps b) and c).

9. The method of claim 5, wherein the adapted MDCK cells have an average doubling time of between about 30 hours and about 35 hours.

10. The method of claim 5, wherein the adapted MDCK cells are suitable for producing virus for a human vaccine, further wherein a virus is produced and the virus maintains antigenicity.

11. A composition comprising adapted MDCK cells produced by the method of claim 5.

12. The composition of claim 11, wherein the adapted MDCK cells have an average doubling time of between about 30 hours and about 35 hours.

13. The composition of claim 11, wherein the adapted MDCK cells are suitable for producing virus for a human vaccine, further wherein the virus maintains antigenicity.

* * * * *